US006966880B2

(12) United States Patent (10) Patent No.: US 6,966,880 B2
Boecker et al. (45) Date of Patent: Nov. 22, 2005

(54) UNIVERSAL DIAGNOSTIC PLATFORM

(75) Inventors: Dirk Boecker, Palo Alto, CA (US); Rick Pittaro, San Carlos, CA (US); Michael Greenstein, Los Altos, CA (US); Michael C. Higgins, Palo Alto, CA (US); Dominique M. Freeman, La Honda, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 379 days.

(21) Appl. No.: 09/981,483

(22) Filed: Oct. 16, 2001

(65) Prior Publication Data

US 2003/0073931 A1 Apr. 17, 2003

(51) Int. Cl.$^7$ .............................................. A61B 5/00
(52) U.S. Cl. ...................... 600/583; 600/573; 128/903
(58) Field of Search ................................ 600/573, 583, 600/584, 300; 128/903, 904; 120/920

(56) References Cited

U.S. PATENT DOCUMENTS

| | | | | |
|---|---|---|---|---|
| 4,731,726 A | * | 3/1988 | Allen, III ................... | 600/300 |
| 5,307,263 A | | 4/1994 | Brown | |
| 5,772,586 A | * | 6/1998 | Heinonen et al. ........... | 600/300 |
| 5,822,715 A | | 10/1998 | Worthington et al. | |
| 5,857,967 A | | 1/1999 | Frid et al. | |
| 5,876,351 A | * | 3/1999 | Rohde ........................ | 600/523 |
| 5,890,128 A | | 3/1999 | Diaz et al. | |
| 5,961,451 A | * | 10/1999 | Reber et al. ................ | 600/322 |
| 5,971,941 A | * | 10/1999 | Simons et al. .............. | 600/573 |
| 6,018,289 A | | 1/2000 | Sekura et al. | |
| 6,066,243 A | | 5/2000 | Anderson et al. | |
| 6,080,106 A | | 6/2000 | Lloyd et al. | |
| 6,085,576 A | | 7/2000 | Sunshine et al. | |
| 6,101,478 A | | 8/2000 | Brown | |
| 6,159,147 A | * | 12/2000 | Lichter et al. ............. | 600/300 |
| 6,295,506 B1 | * | 9/2001 | Heinonen et al. ........... | 702/104 |
| 2002/0002326 A1 | * | 1/2002 | Causey et al. .............. | 600/300 |
| 2002/0177763 A1 | * | 11/2002 | Burns et al. ................ | 600/345 |
| 2003/0083685 A1 | * | 5/2003 | Freeman et al. ............ | 606/181 |

OTHER PUBLICATIONS

"The Universal Connectivity Standard for Point-of-Case," Connectivity Industry Consortium, Draft Technical Specifications, Jan. 8, 2000, Version 0.02, Nov. 20, 2000, 84 pages.
"Handspring Developer Technical Information," www.handspring.com/developers/dev_mechanical.jhtml, Oct. 1, 2001, 5 pages.
Kennelly, Robert J. et al., "Perspectives on Development of IEEE 1073: The Medical Information Bus (MIB) Standard," International Journal of Clinical Monitoring and Computing, 1997, 14:143-149.
"MedVizer, HomeCare Personal Assistant," www.vitelnet.com, copyright 2000 Visual Telecommunications Network, Inc., 1 page.
"MedVizer, Post-Acute Care Solution," www.vitelnet.com, copyright 2000 Visual Telecommunications Network, Inc., 1 page.
"The Memory Stick Advantages," Memory Stick Information for Developers, www.memorystick.org/msinfo/eng/mscon/advan.html, Oct. 1, 2001, 2 pages.
"Memory Stick Duo," Memory Stick Information for Developers, www.memorystick.org/msinfo/eng/ms/duo.html, Oct. 3, 2001, 3 pages.

(Continued)

*Primary Examiner*—Max F. Hindenburg
*Assistant Examiner*—Jonathan Foreman (57) ABSTRACT

A portable medical analyzer comprising a sampling module with a sample port for receiving body fluid, an assay sensor module for analysis of the body fluid, an analytical detector module with detection of information from the assay, and a communications module for transferring the information to a remote location via a wired or wireless network.

43 Claims, 5 Drawing Sheets

OTHER PUBLICATIONS

"New technologies predicted to transform IVD (in vitro diagnostics) market and the role of clinical diagnostics," Clinica, Apr. 12, 1999, 853:28.

"PC Card Technology Primer," The Worldwide Organization for Modular Peripherals, www.pc-card.com/pccard.html, Oct. 1, 2001, 4 pages.

"Distributed Wireless Networks and Healthcare Technologies, Application Position Paper," PsiNaptic Communications Inc., www.psinaptic.com/papers/HealthCare Technology.html, May 7, 2001, 12 pages.

"Mobile Information Technology at the Point-Of-Care," RNpalm, www.rnpalm.com/mitatpoc.html, May 7, 2001, 9 pages.

Goshun Shimosato et al., "On-line Data Management System Using a Portable Blood Gas Analyzer in the Operating Room," Abstract, The Japanese Journal of Anesthesiology, Mar. 2000, 49(3): 319-323.

Carol T. Schembri et al., "Portable Simultaneous Multiple Analyte Whole-Blood Analyzer for Point-of-Care Testing," Clin. Chem., 1992, 38(9):1665-1670.

"CompactFlash," Simple Technology, www.simpletech.com/flash/compactf.html, Oct. 1, 2001, 2 pages.

"SmartMedia Technology Primer," The Worldwide Organization for Modular Peripherals, www.pc-card.com/smartmedia.html, Oct. 1, 2001, 6 pages.

"Wireless Technologies Find Niche in Patient Care," Medical Device & Diagnostic Industry Magazine, an MD&DI Aug. 1998 Column, www.devicelink.com/mddi/archive/98/08/011.html, May 7, 2001, 10 pages.

* cited by examiner

UNIVERSAL DIAGNOSTIC PLATFORM

DESCRIPTION OF THE INVENTION

1. Field of the Invention

The present invention relates to portable medical devices. More particularly to a point-of-care ("POC") medical diagnostic system with communication capabilities.

2. Background of the Invention

Over the past 30 years, the average life expectancy of North Americans has increased by approximately 13 years, contributing to a rapid increase in the number of people over the age of 65. Thus, there has been a dramatic growth in total health care spending as the population ages. As a result, the use of screening and monitoring diagnostics for early intervention, improved treatment and monitoring has become an important aspect of health care.

Technological advances have facilitated the development of easy-to-use, rapid diagnostic devices which can be used in a POC setting, closer to the patient, and that have the ability to pick up disease at an earlier stage. POC testing is attractive because it rapidly delivers results to the medical practitioner and enables faster consultation with the patient. Thus, early diagnosis can enable the practitioner to commence treatment sooner, perhaps leading towards improved patient outcomes. Examples of POC tests include blood chemistry, such as glucose, hematology, immuno-diagnostics, drugs of abuse, serum cholesterol, fecal occult blood test ("FOBT"), pregnancy, and ovulation. In addition many new types of analytics now being carried out in the DNA arena (such as DNA based assays, immuno assays, proteomics and genomics) which are likely candidates for POC testing.

One such example of the potential benefit from a portable medical analyzer in the use of DNA testing is to help doctors prescribe medicine tailored to the particular patient's genotype. Gene-array chip technology determines a patient's genetic information, which a health-care provider may use to classify the patient in particular genotypes. Medications respond differently depending on the particular patient's genotype. By matching the most effective medication for a particular genotype, the patient may receive superior care by avoiding adverse reactions, while maximizing drug efficacy.

A portable medical analyzer provides the additional benefit of facilitating the remote patient monitoring of a patient's medical status. The effectiveness of monitoring systems depends not only on the range of tests reported and their accuracy, but also on the frequency and rapidity of information gathered regarding the patient's health status. A portable medical device can run a range of tests, which cover most of the tests required for diagnosis or therapy monitoring, including blood gases, electrolytes, hematocrit, and various metabolites such as glucose.

Combining biochemical parameter results from the POC device with physiological parameters (such as ECG, respiration rate, temperature and blood pressure) permits integration of vital signs and blood chemistry on a real time basis, for better disease management. Results can then be tracked over time for trend analysis. Portable medical analyzers also have application in the clinical research setting for remote patient evaluation in post surgical recovery, drug therapy and novel pharmaceutical testing using the remote communications ability.

Current POC devices do not provide an integrated solution for patient self-testing to sample acquisition, testing, analysis and connectivity to remote centralized healthcare. Accordingly it is the object of this invention to provide a portable, highly integrated, multi-parameter measurement instrument with IT solutions for data collection, transmission, analysis and on-line decision support. This is achieved by an integrated approach to sample acquisition, a miniaturized multi-parameter low cost test strip or "cartridge," a companion portable instrument and an information solution for connectivity via a wired or wireless network.

SUMMARY OF THE INVENTION

In accordance with the invention, a method and apparatus for utilizing a portable medical analyzer is provided. The method comprises obtaining a body fluid transmission of the fluid to a cartridge, the cartridge comprising at least one assay sensor module, positioning the cartridge into an analytical detector module, where positioning the cartridge breaks a pressure seal on the cartridge causing the body fluid to flow to an assay sensor on the cartridge, using the analytical detector module to detect the results of the assay sensor, connecting the analytical detector module to a communication module, and transferring the results from the analytical detector module to the communication module.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Overview

Figure 1:
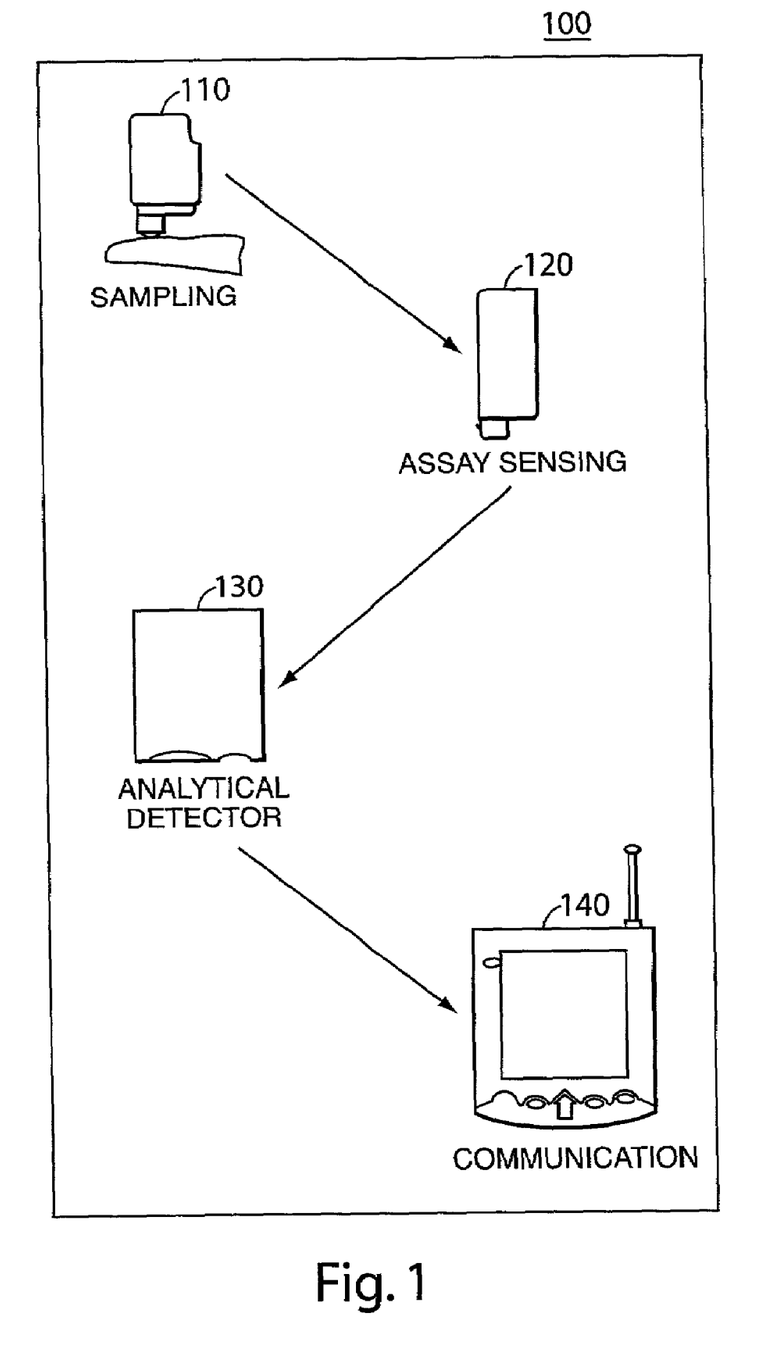
FIG. 1 illustrates an embodiment of sampling, assay sensor, analytical detector, and communication modules according to the present invention.

In accordance with the present invention, a portable medical analyzer is described. One aspect of the present invention is a portable medical analyzer capable of performing a variety of diagnostic tests. Portable may refer to the self-contained nature of the analyzer. Portable may further refer to a hand-held format for the analyzer. As illustrated in FIG. 1, a portable medical analyzer 100 may include a sampling module 110, an assay sensor module 120, an analytical detector (AD) module 130, and a communications module 140.

In one aspect consistent with the present invention, sampling module 110 is a one-step, painless, ergonomic blood sample acquisition module, which provides capillary blood for introduction into an integrated assay sensor module 120. Assay sensor module 120 may be a highly integrated, low-cost, disposable diagnostic cartridge supporting parallel testing of multiple established and emerging diagnostic parameters from body fluids including but not limited to capillary blood, venous blood or blood gases. Analytical detector module 130 employs a modularized hardware technology combining appropriate detection and communication technologies. Analytical detector module 130 module may accept a disposable cartridge or series of disposable cartridges for the analysis of body fluids. Communication module 140, with bi-directional wireless connectivity to an information infrastructure which can provide a gateway to laboratory and clinical information systems, has an information infrastructure for integrating the use of decentralized diagnostic technologies within general patient care processes.

Each type of module can be a removable interchangeable component allowing for module packaging and disposability. Various combinations of sampling, assay sensor, and analytical detector modules could accommodate a very wide range of diagnostic tests, from blood glucose testing to DNA typing. Any of these combinations would be able to utilize a common communication and information infrastructure adding to the flexible nature of this architecture.

Sampling Module

In a portable medical analyzer, sampling module 110 can receive fluids using a variety of methods. The sampling module can acquire a number of body fluids, including but not limited to blood. The fluid can be a liquid and/or a gas. The sampling acquisition port of the portable medical analyzer captures body fluid for testing. The port can receive fluids from a variety of means of sample acquisition and or transfer, including but not limited to, lancing, injection, pipette, intravenous, and catheter. In a non-limiting embodiment, a lancet punctures the skin and a sample collection port, which can be positioned to correspond with the wound created by the lancet, channels the blood to a sample test area or a sample storage chamber. Such channeling can be passive (gravity, capillary flow, etc.) or active (aspiration, vacuum, etc.).

The lancet may be advanced and/or retracted by a variety of mechanical, electrical, electromechanical, piezoelectric, and electromagnetic, or a combination of these types of driving mechanisms. Mechanical driving mechanisms can contain a spring, cam or mass actuators to drive the lancet. These include cantilever springs, diaphragms, coil springs, as well as gravity plumbs to actuate the lancet. Typically, the device is pre-cocked, or the user cocks the device. The device is held against the skin and the user mechanically triggers ballistic launch of the lancet. Other types of driving mechanisms may use electrically based driving and triggering methods, electrical, electromechanical, piezoelectric, and electromagnetic, or a combination of these types of driving mechanisms.

In one embodiment of the invention, a sampling module 110 and assay sensor module 120 are bundled together in one cartridge. This embodiment is described in further detail with the description of FIG. 2 below.

The driving mechanism can be combined in the sampling module, assay sensor module, or analytical detector module. It is desired that the lancet in a module be disposed of with the module for biohazard purposes. It is desired that an expensive mechanism, i.e. electronic, be built into the non-disposable portion of the module e.g. communication module or analytical detector module, where as an inexpensive driving mechanism, i.e. cantilever spring may be built into the disposable module. In the embodiment where the sampling and assay sensor module are combined on one cartridge, such an expensive driving mechanism can be contained on analytical detector module 130, as discussed in FIG. 2.

Alternatively, a sampling module 110 may be used to draw blood into a sample acquisition port, which may be separate from the assay sensor. Such a modular configuration provides flexibility in linking one sampling module 110 with several assay sensors. Blood may thus be allocated to each of the assay sensors thereby, requiring only one lancing event and reducing the donor's discomfort.

Alternately, a sampling module 110 can be coupled to an assay sensor module such that the interface is standardized. For example the Memory Stick Duo® (Sony, Japan) provides a modular solution where the sampling module with a Memory Stick® interface can receive assay sensor modules configured to digital media standards.

Figure 2:
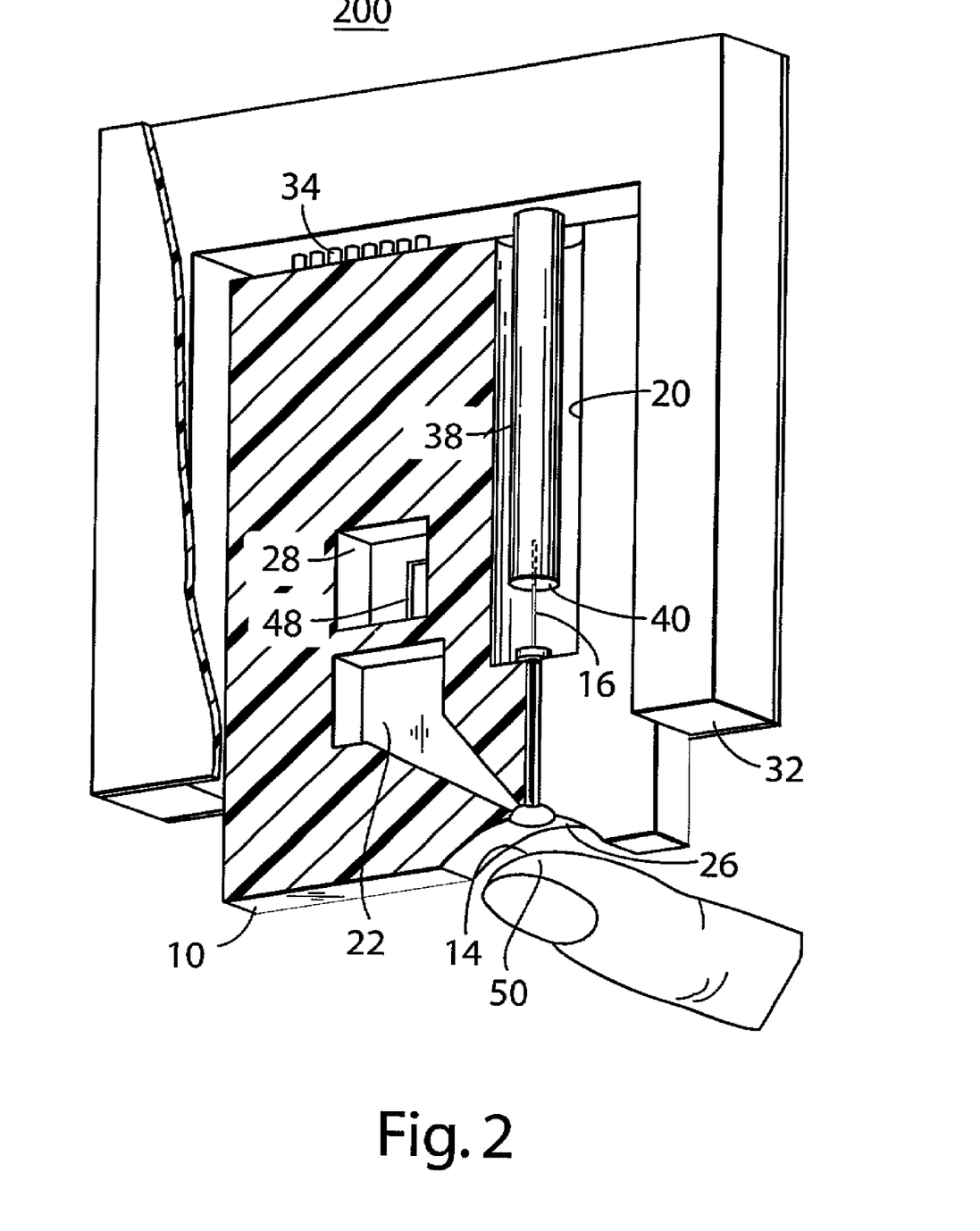
FIG. 2 illustrates a cut-away view of an embodiment of combined sampling and assay sensor modules with an analytical detector module of a portable medical analyzer.

FIG. 2, which illustrates a cut-away view of a portable medical analyzer 200, shows a analytical detector module 130 comprising a slot for cartridge 10, wherein sampling module 110 and assay sensor module 120 are contained. Cartridge 10 is disposable and houses lancet 16. The term "disposable" refers to a fungible feature of the portable medical analyzer, such as a lancet, assay sensor, or cartridge which can be used for one lancing cycle or one analysis and is then discarded. Lancet 16 connects to driver 40 that contains the driving mechanism for advancing and retracting the lancet. Lancet 16 is initially retracted and upon retraction embedded within the cartridge 10. The term "embedded" refers to the lancet being completely shielded by the cartridge when it is not lancing.

Driver 40 plugs into cavity 20 of cartridge 10. Driver 40 may be disposable and attached to the cartridge or reusable and attached to the assay sensor. Reservoir 22 has a narrow opening sample acquisition port 14 on an ergonomically contoured surface 26 for collecting the blood from a donor, such as from finger 50 lanced by lancet 16. Reservoir 22 may fill passively through gravity, or capillary flow, or actively through aspiration or vacuum collect the blood sample.

The cartridge 10 can transport the blood sample through small passages (not shown) using active pumping or passive microfluidics, to a specific localized assay sensor 28 for analyzing the blood, which corresponds to a corresponding location on the analytical detector module 130. The analytical detector module 130 can comprise chemical, physical, optical, electrical or other detecting means of evaluating the blood sample by the assay sensor module 120.

Cartridge 10 is loaded in a slot 32 within analytical detector module 130. The driver 40 contains the driving mechanism 38, which is capable of advancing, stopping, and retracting the lancet 16. The slot 32 also contains the detector 48 for evaluating the blood analysis of the assay sensor 28 on the cartridge 10, which corresponds to the assay sensor 28 on the cartridge 10 which corresponds to detector 48 when the cartridge 10 is loaded into the slot 32. Alternately, cartridge 10 can be designed with an array of testing locations, which contain a variety of assays sensors and correspond to an array of detectors on the analytical detector module 130. Pins 34 on slot 32 provide electrical contact between the cartridge 10 and the analytical detector module 130 to enable identification of the type of assay sensor, and quality control issues (e.g., expiration date of cartridge). Alternatively, cartridge 10 can be in mechanical contact with analytical detector module 120 locking the cartridge 10 in place and puncturing the cartridge 10 to break a vacuum seal and being fluid flow for calibration and create a pressure differential for capillary forces to pull the body fluid sample.

In one embodiment of the invention, the cartridge may be developed on a Memory Stick® (Sony Electronics, Japan) digital media standard interface. Alternative embodiments contemplate other digital medial standard interfaces including but not limited to Compact Flash®, MulitMedia Card®, Secure Digital®, SmartMedia®, or any other removable portable device. The cartridge is of an ultra compact design that has a standard size and connectivity specifications based on the respective standard interface. The removable cartridge can be inserted into an assay detector module 130 with a slot and connector corresponding to the standard for PC cards or Memory Stick Duo® detachable cartridge.

Assay Sensor Module

As used herein, the term "assay sensor" refers to a substrate or location for conducting body fluid analysis, such as but not limited to a biochemical assay. The assay sensor module 120 provides an analytical testing platform for the fluid sample. In a non-binding embodiment, the sampling module and assay sensor are bundled together. Alternatively, the assay sensor may be a separate component. A sample is transported through the assay sensor module to particular assay sensors, through a network of microtubes using active or passive transport.

Figure 3:
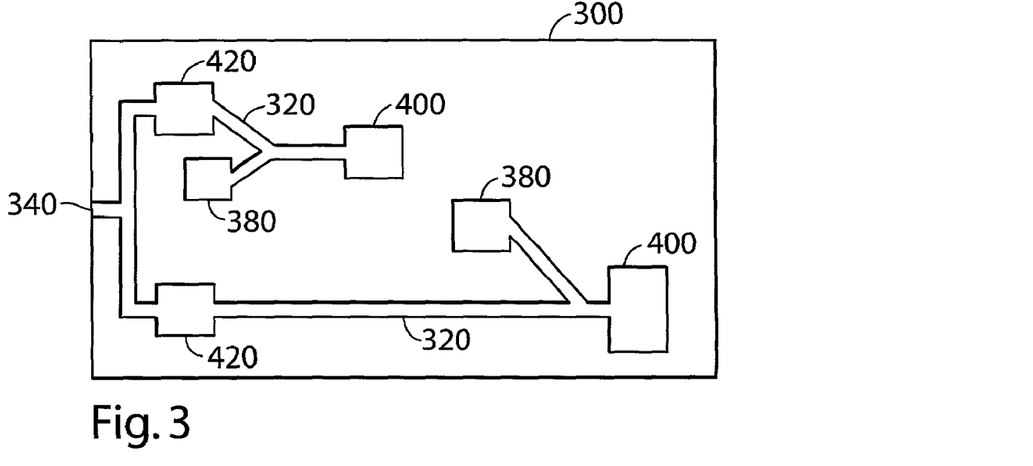
FIG. 3 illustrates a cross-sectional view of an embodiment of an assay sensor module layout.

FIG. 3 illustrates an embodiment of a configuration of multiple assay sensors and tubes for transport in assay sensor module 120. Assay sensor module 120 comprises a cartridge 300, which contains multiple assay sensors 400, each of which correspond to respective detectors (not shown) on analytical detector module 130. Each assay sensor 28 can perform the same analysis, for redundant testing, or a variety of different analysis using reagents stored in reservoirs 380 in the cartridge 300. These reagents are packaged in the cartridge during manufacture, such that the patient does not have to replenish any reagent to conduct the assay. Assay sensors may be chemically or biologically active locations. A number of different types of tests can be performed including blood chemistry, hematology, immunodiagnostics those for drugs of abuse, serum cholesterol, glucose, FOBT, pregnancy, ovulation, along with many new types of analytics now being done in the DNA arena, such as DNA based assays, immuno assays, proteomics and genomics. These tests enable analytical detector module 130 to detect characteristics, or information, about the fluid sample. As used herein, the term "information" refers to data determined as a result of analysis from the analytical testing conducted by the portable medical analyzer.

Blood coming into the cartridge via sample acquisition port 340 is stored in reservoirs 420 so that it can accumulate to volumes appropriate for the relevant assay to be performed. Reagents necessary for the analysis are stored and shielded in reservoirs 380 prior to their use. A system of valves (not shown) keeps the reagents and sample fluid confined to appropriate paths in the cartridge 300. The blood and reagents are transported via active or passive transport through micro tubes 320 to assay sensors 420. The micro tubes 320 may be forked to mix the blood and reagents prior to reaching assay sensors 400. Alternatively, the blood and reagents can mix upon contact with the assay sensor.

Analytical Detector (AD) Module

In the portable medical analyzer, the AD module 130 evaluates the assay sensor in the assay sensor module via detectors, which are associated with the assay sensors. The AD generates signals corresponding to information or characteristics of the assay sensors. The AD module may include signal processing devices and circuitry for the rapid processing of the signals generated by the array of detectors, which correspond to the array of assays. A variety of detectors, including electrical, electrochemical, optical or mechanical can be used to detect results from tests on the assay sensor module. In one embodiment, the AD module can interface with a standard port on a portable computing device such as a laptop computer, a personal digital assistant ("PDA"), or other portable computing device, including but not limited to a Palm™ Handheld, Handspring™ Visor or Compaq iPAQ®. Standard ports include PCMCIA, serial, parallel, USB, IEEE 1394, and other computer connectivity standard ports.

A non-limiting embodiment of the analytical detection module 130 contemplates a PC card platform, such as a Personal Computer Memory Card International Association ("PCMCIA") card or Handspring™ Springboard™ Module. PC cards have standard thicknessses, design and pin assignments. The PC card physical characteristics include a 68 pin physical interface, length 85.6 mm, width 54.0 mm, and a thickness of either 3.3 mm, 5.0 mm, or 10.5 mm, depending on type. PC cards can include a slot for a Memory Stick® or other modular standard for sampling and assay sensor modules, thereby allowing detection and measurement of the assays on the PC card. In one embodiment, many different assays can be performed in the one detection area. The information detected by the analytical detectors contains results from each of these different assays. The thin versatile PC card will be able to both accept the cartridge and plug into a standard communication module for performing tests.

By virtue of the modularity of assay sensing module 120, the analytical detector can be adapted for a wide variety of applications. In addition, by virtue of the modularity of analytical detector module 130, it can plug into a variety of host communication or computational platforms, ranging from PDAs to bench top systems. By utilizing the various combinations of assay sensors and analytical detectors, measurement systems can be configured that range from those suitable for personal use such a glucometer, to instruments for POC hospital application, or even laboratory measurements.

Communication Module

In the portable medical analyzer, a communication module 140 can control both local (onboard) and remote (external) communication. The receiver can be adapted to receive instructions and/or data from external sources. The transmitter can be adapted to transfer the information read from the detector to external databases and systems in remote locations. The communication module 140 can also comprise a display adapted to show the information read from the detector locally to a user via an LCD or other visual indicator. The remote transmission component can be a wireless component. The communication module 140 plays the dual roles of controlling local and remote communication.

One embodiment of communication module 140 can be a PDA, such as a Palm™ PDA, a Handspring™ Visor, or a Compaq iPac®. Communication module 140 can comprise of a standard PDA hardware and software including a processor, display, RF chip, antenna, and an operating system, which may be expanded by using some type of PC card technology. The PDA can be programmed with software to read information from analytical detector module 130, and transmit the information remotely using an industry standard protocol for communication of medical information.

Communication module 140 can have a local storage unit in which the information collected can be stored, such as a localized RAM, i.e. DRAM containing a database of information. The information can also be sent to and stored on a remote database. The remote database can be part of Laboratory Information System, used to manage the information in central and reference laboratories. The remote database can display the information to a clinician, who in turn can analyze the information and send back to the user of the device instruction or comments on the results. Any of these functions can also be performed by a local database. In one embodiment, a communication module in a PDA can transmit and receive information through radio frequency ("RF"), infrared ("IR"), or docking on a cradle as is well known in the art of standard ports for computer peripherals.

In one embodiment, the communication module can direct information to a screen that displays test results to a user. In another embodiment, the module can direct information through a bi-directional wireless system. The communication module 140 can communicate to the user, and communicate with an outside system as well. This connection can be made to a lab, a database, a clinical trial or a Laboratory Information System. The Laboratory Information System is an information management system. The term "information management system" refers to a system that can be used to manage the data between the portable medical analyzer and a centralized means for collecting and processing information for functions including but not limited to qualified user authentication, quality control, quality assurance, quality reporting, clinical processes, such as low impact on workflow, result review, decision support, and business processes (such as submitting information for billing generation, demonstrating cost-effectiveness, supporting practice guidelines, and direct marketing). The information and instructions transmitted to the portable medical analyzer can be directed to the particular user based on personal identification and security information.

Technically, the analyzer has many key features including reliability, security and confidentiality, content distribution, and functionality distribution (such as a application service provider). The analyzer can be connected to a central system, or it can stand alone. Once connected to a system, synchronization can take place. At the remote database end of the system, security and confidentiality are supported by creating authorization and authentication schemes to limit the access to data. The functionality distribution includes the creation of multi-tier disruption models, which may include localized computation or centralized server based computation. The functionality of the system is adaptive based on the availability of local or remote resources.

In one embodiment, the data collected can be used for blind testing. A brokering system can be structured based on the collected personal medical records. The confidentiality of the system allows individuals to sell their medical data anonymously to customers. The customers can then use the data to develop medical technology or evaluate a heath care system.

In another embodiment, a patient management system can be adapted to application distribution and information management. The system uses the portable medical analyzer and provides health care organizations with information integration and access to administrative, data management and decision support applications at the point of care.

In another embodiment, the analyzer can be adapted to receive instructions from an administration system to automate processes such as calibration. The device can be in constant communication with a central hospital server system. At regular intervals the server can send a communication to the device that calibration is necessary. In one embodiment, the user can take a calibration cartridge and insert it into the device for calibration. The server can then either confirm that the device is calibrated or tell the user the device must be recalibrated manually.

In another embodiment, the analyzer can be used for viewing of historical data such as previous results and patient trends. The analyzer can download past patient results, or store past patient results locally, and after testing show the patient not only the current results but also where they fall within historical trends.

In another embodiment the analyzer can be a part of the Universal Connectivity Standard for Point-of-Care, for which further information may be forward at www.pocci-c.org. Using the connectivity standards, the device may be connected to both other devices and major medical or hospital systems. The communication can take place via an IR port, wireless networks or through connected phone lines.

In another embodiment, an analyzer connected to an LIS can compare results from diagnostic tests run in the laboratory of full-size analyzers and develop correlation tables between results from the portable medical analyzer and the laboratory results.

Method of Use

Figure 4:
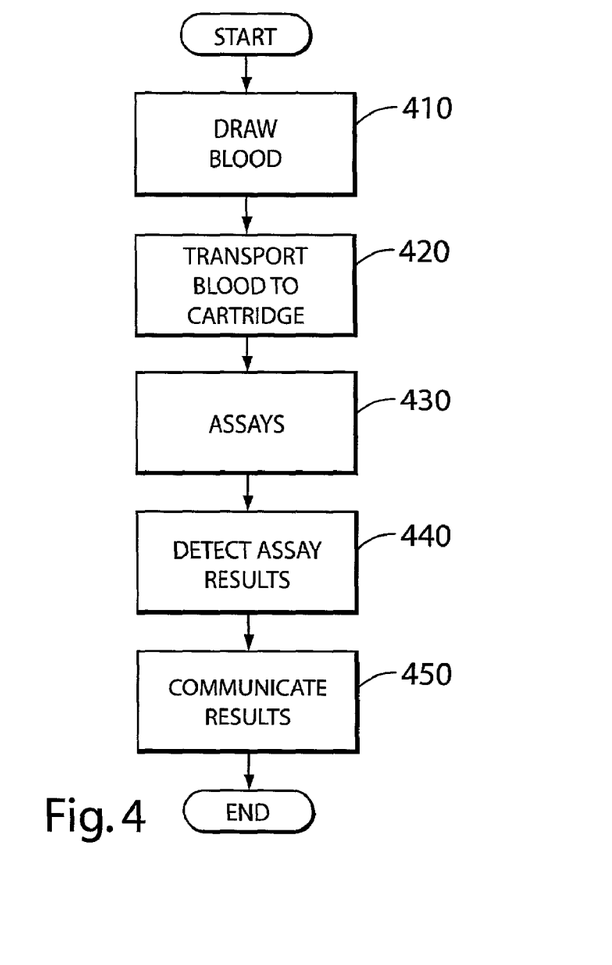
FIG. 4 illustrates a flow chart of a method of operation for an embodiment of a portable medical analyzer.

FIG. 4 illustrates a flow diagram of an embodiment of a method for POC diagnosis using a portable medical analyzer as described in FIG. 1. Sampling module 110 is integrated into assay sensor module 120 in the form of a cartridge with a lancet. The user takes the cartridge and presses it against a finger. The driving mechanism trigger from the pressure of the trigger or a button on the analyzer. The driving mechanism propels the lancet, which lances the skin and draws body fluid (step 410). Once the cartridge is locked into analytical detector a pressure seal is broken causing calibration fluid, reagents and sampled body fluid to flow through the cartridge (step 420). The body fluid flows to the location of the assays on the cartridge, allowing for the chemical analysis by sensor and detection by detectors on the analytical detector module (step 430).

In another embodiment, the flow calibration fluid is simultaneously with body fluid sample. Analytical detector 130 can be connected to communication module 140 through a standardized port. When connected, communication module can provide extra mechanical and electrical power to analytical detector 130. Once powered, analytical detector 130 can quantify the results of the chemical analysis on the assay sensor module (step 440). The results are then transferred from analytical detector module 130 to communication module 140 through the standard pin connections (step 450). Communication module 140 can display the results locally for a user and/or transfer the results immediately or at a later time to a central database in a remote location. The entire process, from lancing to results may take as little as a few minutes.

Figure 5:
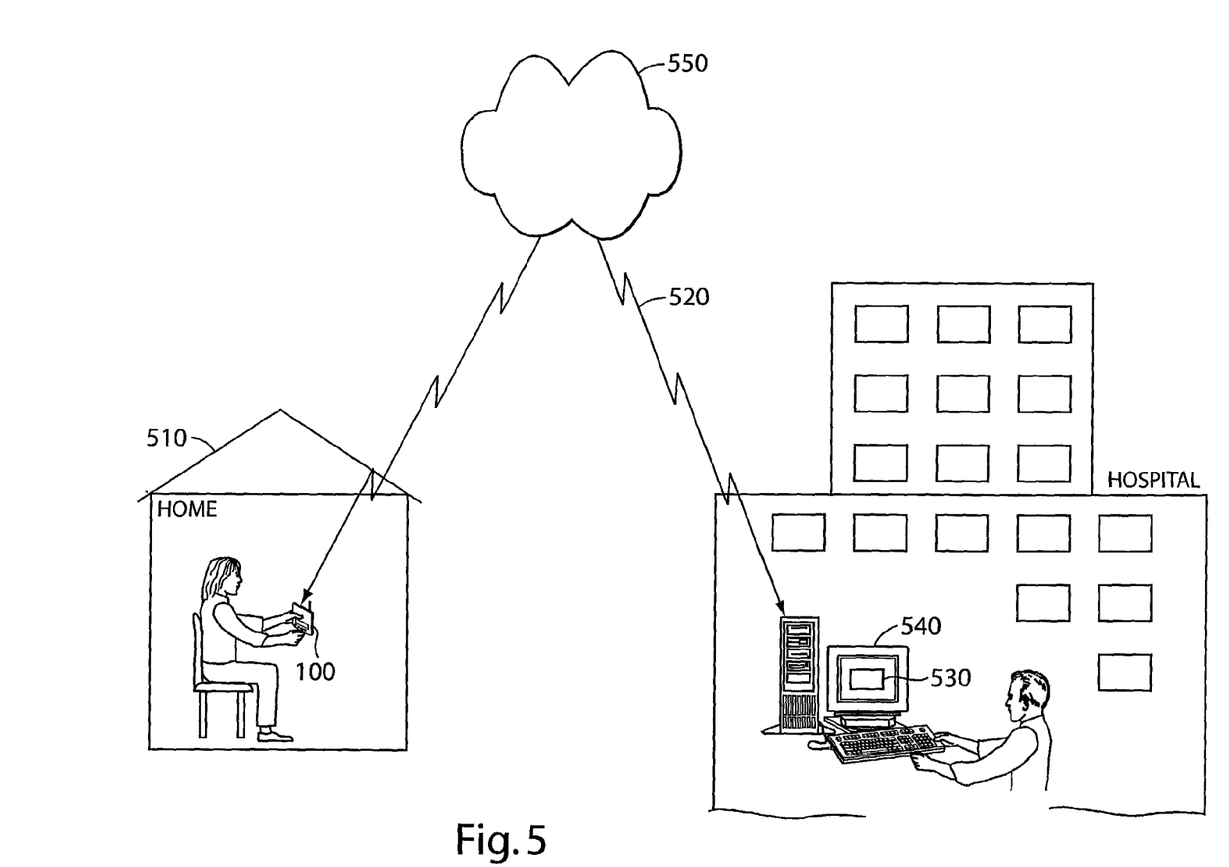
FIG. 5 illustrates a block diagram of an embodiment of a communication module within a network environment.

FIG. 5 illustrates an embodiment of the communication module within a network environment. An individual in a home setting 510 with portable medical analyzer 100 can use the analyzer to sample blood. Within the device a series of steps are performed to gather data. Once the data is gathered, it is wirelessly transmitted 520 through a communication network 550 e.g. cellular, microwave, satellite, Internet, etc. to a remote system 570 in the hospital setting 560. The remote system can include computer 540 with a receiver and decoder that places the data into a remote database 530. The computer 540 hosting the remote database can then process and display the information. Either a computer program or an operation at the computer terminal can send information back to the device, such as treatment information. Alternately, the computer 540 can be a network server operating communication network 550 as a Wide Area Network (WAN).

Figure 6:
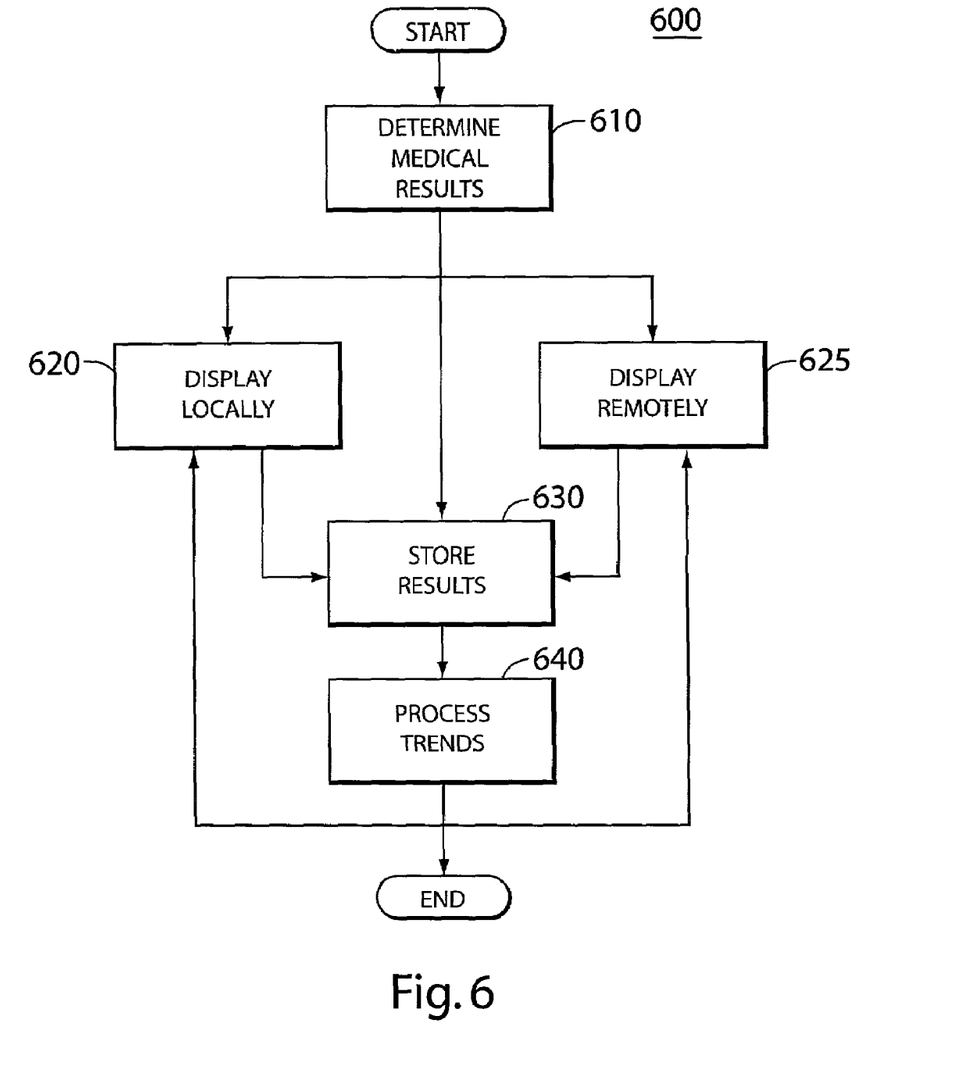
FIG. 6 illustrates a flow chart of an embodiment of a method of operation for a portable medical analyzer.

FIG. 6 is a flow diagram illustrating a method 600 of operation of an embodiment of a communication module within a network environment. In method 600, once the analytical detector determines medical results (step 610), one or a combination (or more) of these steps can result. The results can be displayed locally (step 620), the results can be displayed remotely (step 625) or the results can be stored (step 630) either locally or remotely or both. If the results are displayed, this can be the end of the process, or then the results can be stored. Once the results are stored, the computer can process the results and create result trends (step 640). After the processing of trend results, the trends can be displayed locally, displayed remotely, or not displayed at all. Method 600 illustrates the various methods by which the analyzer can communicate and interact with a user and a network.

Although what has been described is aimed at analysis of body fluids, this concept is easily extended. Analytical detector modules could be developed to provide other diagnostic measurements such as ECG, or temperature etc. These measurements would then take advantage of the same communication module and communication network to transmit information.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A portable medical analyzer comprising:
a sampling module comprising a lancet, a driving mechanism, and a sample port, wherein said sampling port receives at least one body fluid directly from a tissue punctured with said lancet driven by said driving mechanism;
an assay sensor module housed in a cartridge, said cartridge comprising an interface with said sample port and at least one passage way to transport said body fluid to at least one assay sensor in said assay sensor module;
an analytical detector module comprising at least one analytical detector positioned to correspond to said assay sensor, said detector is adapted to detect information from said assay sensor; and
a communication module adapted to communicate with an information management system;
wherein said sampling module is housed in said cartridge; and
wherein said analytical detector module is adapted to couple with said communication module via a PCMCIA interface.

2. A portable medical analyzer comprising:
a sampling module comprising a lancet, a driving mechanism, and a sample port, wherein said sampling port receives at least one body fluid directly from a tissue punctured with said lancet driven by said driving mechanism;
an assay sensor module housed in a cartridge, said cartridge comprising an interface with said sample port and at least one passage way to transport said body fluid to at least one assay sensor in said assay sensor module;
an analytical detector module comprising at least one analytical detector positioned to correspond to said assay sensor, said detector is adapted to detect information from said assay sensor; and
a communication module adapted to communicate with an information management system;
wherein said sampling module is housed in said cartridge; and
wherein said cartridge is adapted to a digital media standard interface, said analytical detector module is adapted to couple with said cartridge via said digital media standard interface, said analytical detector module is adapted to a standard port, and said communication module is adapted to couple with said analytical detector module via said standard port.

3. A method for portable medical analysis comprising:
obtaining a body fluid from a tissue punctured with a lancet, the lancet being driven by a driving mechanism, wherein the body fluid from the tissue flows directly into a cartridge having said lancet;
housing said body fluid within the cartridge comprising an assay sensor module;
positioning said cartridge into an analytical detector module;
obtaining information from said analytical detector module;
displaying said information locally on a display within said communication module; and
transferring said information to a remote location via a communication module;
wherein positioning said cartridge further comprises breaking a pressure seal on said cartridge, said breaking adapted to transfer said body fluid to at least one assay sensor in said assay sensor module.

4. A portable medical analyzer comprising:
a sampling module comprising a lancet, a driving mechanism, and a sample port, wherein said sampling port receives at least one body fluid from a tissue punctured with said lancet driven by said driving mechanism, said sampling module is housed in said cartridge;
an assay sensor module housed in a cartridge, said cartridge comprising an interface with said sample port and at least one passage way to transport said body fluid to at least one assay sensor in said assay sensor module;
an analytical detector module comprising at least one analytical detector positioned to correspond to said assay sensor, said detector is adapted to detect information from said assay sensor, said analytical detector module is adapted to couple with a communication module via a PCMCIA interface; and
said communication module adapted to communicate with an information management system.

5. A portable medical analyzer comprising:
a sampling module comprising a lancet, a driving mechanism, and a sample port, wherein said sampling port receives at least one body fluid from a tissue punctured with said lancet driven by said driving mechanism, said sampling module is housed in a cartridge,
an assay sensor module housed in said cartridge, said cartridge comprising an interface with said sample port and at least one passage way to transport said body fluid to at least one assay sensor in said assay sensor module;

an analytical detector module comprising at least one analytical detector positioned to correspond to said assay sensor, said detector is adapted to detect information from said assay sensor; and a communication module adapted to communicate with an information management system, wherein said cartridge is adapted to a digital media standard interface, said analytical detector module is adapted to couple with said cartridge via said digital media standard interface, said analytical detector module is adapted to a standard port, and said communication module is adapted to couple with said analytical detector module via said standard port.

6. A method for portable medical analysis comprising:

obtaining a body fluid directly from a tissue puncture created by a lancet, wherein the lancet is driven outward from a cartridge by a lancet driver and wherein the body fluid from the tissue puncture flows into the cartridge;

housing said body fluid within the cartridge, said cartridge having an assay sensor;

obtaining information regarding said body fluid in the cartridge from an analytical detector in communication with the assay sensor; and transferring said information to a remote location via a communication module;

wherein a pressure seal on the cartridge is broken, via interface with the analytical detector, during transfer of the body fluid to the assay sensor.

7. A method as in claim 6 further comprising displaying said information locally on a display coupled to said communication module.

8. A method as in claim 6 wherein said communication module is adapted to transfer said information to a remote location.

9. A method as in claim 6 wherein said cartridge includes a plurality of assay sensors, each of said sensors performing the same analysis on the body fluid.

10. A method as in claim 6 wherein said communication module uses at least one interface chosen from radio frequency, infrared and standard ports.

11. A method as in claim 6 wherein said lancet is driven by an electromechanical lancet driver.

12. A method as in claim 6 wherein said lancet is driven by an electrical lancet driver.

13. A method as in claim 6 wherein said cartridge includes a plurality of assay sensors, each of said sensors performing a variety of different analysis on the body fluid.

14. A method as in claim 13 wherein at least one of said sensors provides analysis for one of the following: a blood chemistry, hematology, immuno-diagnostics those for drugs of abuse, serum cholesterol, glucose, FOBT, pregnancy, ovulation, DNA based assays, immuno assays, proteomics and genomics.

15. A method for portable medical analysis comprising:
obtaining a body fluid;
housing said body fluid within a cartridge comprising art assay sensor module;
positioning said cartridge into an analytical detector module, wherein positioning said cartridge comprises breaking a pressure seal on said cartridge, said breaking adapted to transfer said body fluid to at least one assay sensor in said assay sensor module;
obtaining information from said analytical detector module;
displaying said information locally on a display within communication module; and
transferring said information to a remote location via the communication module.

16. The method of claim 15 wherein the communication module includes a receiver adapted to communicate with a remote location.

17. The method of claim 15 wherein the communication module includes one or more of the following: a processor, a display, a radio frequency chip, an antenna, memory containing an operating system, RAM, DRAM or a PCMIA interface.

18. The method of claim 15 wherein the positioning of the cartridge into the analytic detector module provides connection via a digital media standard interface.

19. The method of claim 15 wherein the positioning of the cartridge into the analytic detector module provides connection via a PCMCIA interface.

20. The method of claim 15 wherein the cartridge is adapted to a digital media standard interface, wherein the positioning of the cartridge into the analytic detector module provides connection via a digital media standard interface, wherein the analytical detector module is adapted to a standard port, and wherein the communication module is adapted to couple with said analytical detector module via the standard port.

21. The method of claim 15 wherein the processing of information is accomplished via an information management system that includes procedures for administering the medical analysis.

22. The method of claim 15 wherein the sensor provides analysis for one of the following: a blood chemistry, hematology, immuno-diagnostics those (or drugs of abuse, serum cholesterol, glucose, FOBT, pregnancy, ovulation, DNA-based assays, immuno assays, proteomics or genomics.

23. The method of claim 15 wherein the sensor provides analysis for one or more of the following: a blood chemistry, hematology, immuno-diagnostics those for drugs of abuse, serum cholesterol, glucose, FOBT, pregnancy, ovulation, DNA-based assays, immuno assays, proteomics or genomics.

24. The method of claim 15 further comprising the step of storing the information locally in an information storage unit associated with the portable medical analyzer.

25. The method of claim 15 wherein the communication module includes a transmitter and a receiver, both in communication with an information management system, wherein the information management system is a centralized means for collecting and processing information for functions.

26. The method of claim 15 further comprising acquiring historical data locally via the communication module.

27. The method of claim 15 further comprising storing historical data locally in association with the communication module, the analytical detector module, the cartridge or the assay sensor module.

28. The method of claim 15 further comprising displaying historical data locally on the display.

29. The method of claim 15 wherein the transferring of information is accomplished via an information management system.

30. The method of claim 15 wherein the processing of information is accomplished via an information management system that includes procedures for brokering medical data.

31. The method of claim 15 wherein the processing of information is accomplished via an information management system that includes patient management procedures.

32. The method of claim 15 wherein the processing of information is accomplished via an information management system that includes procedures for administering the medical analysis.

33. The method of claim 15 wherein the communication module includes a transmitter.

34. The method of claim 33 wherein the transmitter is adapted to one or more of interface selected from the group consisting of radio frequency, infrared and standard ports.

35. The method of claim 33 wherein the transmitter is adapted to communicate with a remote database.

36. The method of claim 15 wherein the cartridge houses a sampling module.

37. The method of claim 36 wherein the positioning of the cartridge into the analytic detector module provides connection via a digital media standard interface.

38. The method of claim 36 wherein the positioning of the cartridge into the analytic detector module provides connection via a PCMCIA interface.

39. The method of claim 36 wherein the cartridge is adapted to a digital media standard interface, wherein the positioning of the cartridge into the analytic detector module provides connection via a digital media standard interface, wherein the analytical detector module is adapted to a standard port, and wherein the communication module is adapted to couple with said analytical detector module via the standard port.

40. The method of claim 15 wherein said cartridge includes a plurality of assay sensors, each of said sensors performing the same analysis on the body fluid.

41. The method of claim 40 wherein at least one of said sensors provides analysis for one of the following: a blood chemistry, hematology, immuno-diagnostics those for drugs of abuse, serum cholesterol, glucose, FOBT, pregnancy, ovulation, DNA based assays, immuno assays, proteomics and genomics.

42. The method of claim 15 wherein said cartridge includes a plurality of assay sensors, and two or more of the sensors perform different analyses on the body fluid.

43. The method of claim 42 wherein at least one of said sensors provides analysis for one of the following: a blood chemistry, hematology, immuno-diagnostics those for drugs of abuse, serum cholesterol, glucose, FOBT, pregnancy, ovulation, DNA based assays, immuno assays, proteomics and genomics.

* * * * *